(12) United States Patent
Layzell et al.

(10) Patent No.: US 7,162,834 B2
(45) Date of Patent: Jan. 16, 2007

(54) METHODS FOR ENHANCING PLANT GROWTH USING HYDROGEN GAS

(75) Inventors: David B. Layzell, Kingston (CA); Zhongmin Dong, Halifax (CA); Lishu Wu, Hubei (CN)

(73) Assignee: Queen's University at Kingston, Kingston (CA)

( * ) Notice: Subject to any disclaimer, the term of this patent is extended or adjusted under 35 U.S.C. 154(b) by 0 days.

(21) Appl. No.: 11/045,473

(22) Filed: Jan. 31, 2005

(65) Prior Publication Data

US 2005/0178057 A1 Aug. 18, 2005

Related U.S. Application Data

(60) Division of application No. 10/040,469, filed on Jan. 9, 2002, now Pat. No. 6,848,212, and a continuation of application No. PCT/CA00/00863, filed on Jul. 24, 2000.

(60) Provisional application No. 60/146,322, filed on Jul. 30, 1999.

(51) Int. Cl.
*A01G 7/06* (2006.01)
*A01C 21/00* (2006.01)

(52) U.S. Cl. ..................... 47/58.1 SC; 71/1
(58) Field of Classification Search ........... 47/58.1 SC, 47/58.1 R; 71/7, 8, 9, 10, 1
See application file for complete search history.

(56) References Cited

U.S. PATENT DOCUMENTS

| | | | |
|---|---|---|---|
| 291,841 A | * 1/1884 | Giles | ............ 188/148 |
| 2,088,869 A | 8/1937 | Porter | |
| 2,767,072 A | * 10/1956 | Coanda | ............ 71/7 |
| 2,869,998 A | 1/1959 | Vierling | |
| 3,359,091 A | 12/1967 | Clevenger | |
| 3,550,319 A | * 12/1970 | Gaines, Jr. | ............ 47/79 |
| 3,661,549 A | 5/1972 | Freytag et al. | |
| 5,288,296 A | * 2/1994 | McCabe et al. | ............ 504/117 |
| 5,299,383 A | 4/1994 | Takakura et al. | |

(Continued)

FOREIGN PATENT DOCUMENTS

JP 8-140471 * 6/1996

(Continued)

OTHER PUBLICATIONS

Conrad, R., et al., "Contribution of hydrogen production by biological nitrogen fixation to the global hydrogen budget." *J. Geophysical Research* 85: 5493-5498 (1980).

(Continued)

*Primary Examiner*—Jeffrey L. Gellner
(74) *Attorney, Agent, or Firm*—Stephen J. Scribner; Carol Miernicki Steeg (57) ABSTRACT

This invention provides methods of enhancing plant growth or yield, comprising exposing soil to hydrogen gas ($H_2$), and growing plants in the soil. The $H_2$ gas employed can be generated by electrolysis of water, produced by $H_2$ evolving microorganisms, and/or produced by legumes. In accordance with the invention, soil can be exposed to $H_2$ and plants then grown in it, or $H_2$ can be applied directly to soil in which plants are already growing. In one embodiment, the invention comprises obtaining an aqueous extract from $H_2$-treated soil, and applying the extract to soil, seeds, and or plant roots.

15 Claims, 2 Drawing Sheets

U.S. PATENT DOCUMENTS

| | | | | |
|---|---|---|---|---|
| 5,511,905 | A | * | 4/1996 | Bishop et al. ............... 405/59 |
| 5,566,627 | A | | 10/1996 | Pryor |
| 5,601,236 | A | * | 2/1997 | Wold ............................ 239/63 |
| 5,602,296 | A | * | 2/1997 | Hughes et al. ............. 588/316 |
| 5,695,541 | A | * | 12/1997 | Kosanke et al. ................ 71/7 |
| 5,803,664 | A | * | 9/1998 | Kawabata et al. ....... 405/128.5 |
| 5,965,801 | A | | 10/1999 | Layzell et al. |

FOREIGN PATENT DOCUMENTS

| WO | WO 98/44802 | 10/1998 |
|---|---|---|

OTHER PUBLICATIONS

Dugnani, L., et al., "Biological oxidation of hydrogen in soils flushed with a mixture of $H_2$, $CO_2$, $O_2$ and $N_2$." *FEMS Microbiology Ecology* 38: 347-351 (1986).

Eisbrenner, G., et al., "Aspects of hydrogen metabolism in nitrogen-fixing legumes and other plant-microbe associations." *Ann. Rev. Plant Physiol.* 34: 105-136 (1983).

La Favre, J.S., et al., "Conservation in soil of $H_2$ liberated from $N_2$ fixation by Hup nodules." *Applied and Environmental Microbiology* 46: 304-311 (1983).

Nelson, L.M., "Hydrogen recycling by *Rhizobium leguminosarum* isolates and growth and nitrogen contents of pea plants (*Pisum sativum L.*)." *Applied and Environmental Microbiology* 45:856-861 (1983).

Popelier, F., et al., "Soil $H_2$-uptake in relation to soil properties and rhizobial $H_2$-production." *Plant and Soil* 85: 85-96 (1985).

Schubert, K.R., et al., "Hydrogen evolution: A major factor affecting the efficiency of nitrogen fixation in nodulated symbionts." *Proc. Nat. Acad. Sci. U.S.A.* 73: 1207-1211 (1976).

Schuler, S., et al., "Hydrogen oxidation in soil following rhizobial $H_2$ production due to $N_2$ fixation by a *Vicia faba-Rhizobium leguminosarum* symbiosis." *Biol. Fertil. Soils* 11: 190-195 (1991).

Schuler, S., et al., "Hydrogen oxidation activites in soil as influenced by pH, temperature, moisture, and season." *Biol. Fertil. Soils* 12: 127-130 (1991).

* cited by examiner

METHODS FOR ENHANCING PLANT GROWTH USING HYDROGEN GAS

RELATED APPLICATIONS

This application is a division of U.S. patent application Ser. No. 10/040,469, filed on Jul. 24, 2000, now U.S. Pat. No. 6,848,212, and claims the benefit of the filing date of U.S. Provisional Patent Application No. 60/146,322, filed on Jul. 30, 1999, the contents of which are incorporated herein by reference in their entirety.

FIELD OF THE INVENTION

This invention relates to methods for enhancing plant growth or yield. In particular, this invention relates to methods for enhancing plant growth or yield by exposing soil to hydrogen gas ($H_2$).

BACKGROUND OF THE INVENTION

Modern agriculture relies on extensive use of fertilizers and chemical pesticides to maintain high levels of production in the face of a rising world population, expanding urbanization and land degradation. However, widespread use of agricultural chemicals has led to environmental problems such as toxicity and eutrophication, resulting in greater interest in alternative approaches to enhancing and sustaining agricultural productivity.

Soil microflora (e.g., bacteria, fingi) can improve plant growth through providing plant-available nutrients (i.e., nutrients in a form that the plant can use), increasing the uptake of mineral nutrients and protecting plants against pests and diseases (Hart et al. 1986; Williams and Sparling 1988; Insam et al. 1991; Srivastava and Singh 1991; Bankole and Adebanjo 1996; Omar and AbdAlla 1998). For example, mycorrhizal association with plant roots is known to enhance growth by assisting with the uptake of phosphorours and other nutrients. Alternatively, a number of plant growth promoting rhizobacteria (PGPR) have been identified which stimulate plant growth by preventing phytopathogens from inhibiting plant growth and development (O'Sullivan and O'Gara 1992; Sivan and Chet 1992; Cook 1993; Glick 1995) or by providing plants with compounds such as fixed nitrogen, phosphate, phytohormones, or solubilized iron from soil (Brown 1974; Kloepper et al. 1988, 1989; Glick 1995).

It has long been known that enhancement of plant growth may be carried out naturally through crop rotation or intercropping with plants belonging to the legume family (e.g., clover, alfalfa). Typically, this can lead to significant increases in the growth and yield of the non-legume crop. Legume plants form a symbiotic relationship with certain soil microorganisms resulting in the formation of structures called nodules on their roots. Root nodules use plant-derived carbohydrate and the enzyme nitrogenase to convert (fix) atmospheric dinitrogen ($N_2$) gas into a reduced form of nitrogen (N) that plants can use, with hydrogen gas ($H_2$) as a byproduct. As a result, legumes are able to grow without nitrogen fertilizer, an expensive agricultural input that has many environmental costs. Interestingly, only about 25% of the increase in the growth of the non-legume crop can be attributed to improved N nutrition. The remaining 75% of the effect has eluded explanation (Bolton et al. 1976; Hesterman et al. 1986; Fyson and Oaks 1990), although factors that have been proposed include: breaking disease cycles, opening channels for root growth through the hard-pan, and altering the balance of micronutrients in the soil.

OBJECT OF THE INVENTION

It is an object of the present invention to provide a method for enhancing plant growth or yield by exposing soil to hydrogen gas ($H_2$).

SUMMARY OF THE INVENTION

According to a broad aspect of the invention, there is provided a method for enhancing plant growth or yield, comprising exposing soil to $H_2$ gas, and growing plants in the soil. The soil exposed to $H_2$ can also be combined with soil not exposed to $H_2$, and plants grown in the thus combined soil. In a preferred embodiment, the amount of the combined soil which is the soil exposed to $H_2$ is between about 5% and 100%, by volume. Further, the soil exposed to $H_2$ can be combined with soil in which plants are already growing.

In accordance with the invention, the $H_2$ gas employed can be generated by the electrolysis of water. In other embodiments, the $H_2$ gas is generated by providing an electrical current in the soil so as to generate $H_2$ directly within the soil, or by $H_2$ evolving microorganisms. In the latter case, the $H_2$ evolving microorganisms can also be $N_2$ fixing microorganisms. The $N_2$ fixing microorganisms can be symbiotic nitrogen-fixing bacteria associated with legumes, or soil bacteria.

In accordance with the invention, the method further comprises the step of placing the soil to be exposed to $H_2$ in a container that minimizes the diffusion of $H_2$ therefrom, and applying $H_2$ to the soil in the container. In an alternative embodiment, the method further comprises the step of covering the soil to be exposed to $H_2$ with a membrane having a low permeability to $H_2$, and providing $H_2$ below the membrane, wherein at least a portion of the exposure of the soil to $H_2$ occurs beneath the membrane.

In accordance with another aspect of the invention, there is provided a method for enhancing plant growth or yield, comprising: obtaining a soil sample; and exposing the soil sample to $H_2$ gas; wherein said exposure of soil to $H_2$ enhances the ability of soil microorganisms to oxidize $H_2$; and wherein the enhanced ability of microorganisms potentiates enhanced growth or yield of plants growing in said soil.

According to another embodiment, the method further comprises isolating said microorganisms, and applying the microorganisms to soil, seeds, or plant roots; wherein said application of microorganisms potentiates enhanced growth or yield of plants. In yet another embodiment, the microorganisms are cultured and applied to soil, seeds, or plant roots.

According to a further aspect of the invention, there is provided a method for enhancing plant growth or yield, comprising exposing soil to $H_2$ gas, obtaining an extract of the soil exposed to $H_2$ gas, and applying the extract to seeds, plant roots, or soil. In one embodiment, the extract is an aqueous extract.

BRIEF DESCRIPTION OF THE DRAWINGS

Embodiments of the invention will now be described, by way of example, with reference to the accompanying drawings, wherein.

DETAILED DESCRIPTION OF THE INVENTION

In root nodules of legumes, hydrogen gas ($H_2$) is a byproduct of nitrogen fixation, claiming about 33% of the reducing power and ATP that flows to the nitrogenase enzyme (the other 67% is used to reduce $N_2$). In some legume symbioses, bacteria also produce uptake hydrogenase (HUP), an enzyme which is able to oxidize the $H_2$ (forming water) and thereby recover the reducing power used in $H_2$ production. However, many symbioses, especially those used in temperate agriculture, lack uptake hydrogenase (i.e., HUP-symbioses), and the $H_2$ produced by the nitrogenase diffuses out of the nodule into the soil.

$N_2$ fixation and $H_2$ production are energetically expensive processes, consuming about 15% of the carbohydrates that the legume plant produces through photosynthesis. It is estimated that the $H_2$ released into soil by legumes such as HUP− alfalfa grown in Canada represents an energy source equivalent to 5 to 6% of the crop's net photosynthesis. It is not understood why evolutionary processes, plant breeding of agricultural crops, or selection of optimal $N_2$ fixing bacteria has not reduced this energy loss in all legumes.

The researchers in the present invention have been investigating what happens to the $H_2$ that is produced by HUP− legume nodules. The present invention is based, at least in part, on the discovery that exposure of soil to $H_2$ has a plant growth or yield enhancing effect. Essentially, the inventors have discovered that the $H_2$ produced as a by-product of nitrogen fixation by legume nodules is responsible for a substantial portion of the growth or yield enhancing effects of legume soils. Typically, plant growth, measured as shoot and/or root length or fresh or dry biomass, is enhanced by 10 to 30% or more. It is believed that the plant growth promoting effect arises as a result of one or more of the following: $H_2$-oxidizing microorganisms in the soil effecting an improvement in the nutrient status of soil that is beneficial to plant growth; an increase in the population of one or more species of plant growth enhancing microorganisms such as plant growth promoting rhizobacteria (PGPR); enhancing the plant's disease resistance; and enhancing the plant's growth regulator balance.

As used herein, the term "enhanced plant growth" refers to the ability of a plant, growing in soil exposed to $H_2$, to grow faster, larger, or more vigourously relative to a plant growing in soil not exposed to $H_2$.

As used herein, the term "enhanced plant yield" refers to the ability of a plant, growing in soil exposed to $H_2$, to produce more or larger flowers, seeds, fruit, leaves, roots (biomass) relative to a plant growing in soil not exposed to $H_2$. It should be noted that a plant exhibiting enhanced yield may be the same size (e.g., height) or even smaller than a plant not exhibiting enhanced yield, but the former has more flowers, seeds, fruit, or biomass. Plants with increased biomass are more resistant to pathogens, and in general have greater commercial value.

The discovery that $H_2$ treated soils enhance plant growth might account for the observed beneficial effects of legumes used in rotations with cereals and other crops. If so, $H_2$ fertilization of soils appears to achieve the beneficial effects of crop rotation, without the need to implement actual crop rotation. This discovery also helps to account for the evolutionary questions surrounding why HUP− symbioses have thrived when there are genes (in many cases within the same genus and species) for the more energy-efficient HUP+ symbioses. Perhaps the plant growth advantages of the HUP− symbioses offset the greater energy efficiency of the HUP+ symbioses.

Previous investigations have examined $H_2$ in soil and have shown that soils can be the dominant sink of $H_2$ (Conrad et al. 1980), and that part of the $H_2$ produced by the nitrogenase of legumes is rapidly oxidized by soil microorganisms within a few cm of the legume nodules (Schuler et al. 1991a). Despite numerous attempts (Conrad et al. 1979a, b, 1983; Haring and Conrad 1994; Haring et al. 1994; Kluber et al. 1995; Lechner and Conrad 1997), the microorganisms responsible for $H_2$ oxidation in soils have yet to be identified and one study (Conrad 1988) questioned whether the $H_2$ oxidation was, in fact, biological or chemical. Popelier et al. (1985), using a closed gas exchange system, found a highly significant positive correlation between the microbial biomass of the soil and the soil $H_2$ uptake rate, and Schuler et al. (1991b) showed that environmental factors such as temperature, soil water content, and oxygen concentration influence soil $H_2$ uptake activity. La Favre et al. (1983) showed that $H_2$ production from legume nodules induced $H_2$ oxidation capacity of the soil, and that this capacity and the number of $H_2$ oxidizing bacteria decreased exponentially with distance from the nodule. Other studies have confirmed that treatment of soil with $H_2$ results in an enrichment of the aerobic, autotrophic $H_2$-oxidizing microflora (Dugnani et al. 1986). It should be noted that, as used herein, the terms "$H_2$ oxidation" and "$H_2$ uptake" refer to the same process.

Indeed, using soils from three continents (localities at Kingston, Ontario, Canada; Montreal, Quebec, Canada; Halifax, Nova Scotia, Canada; Nedlands, Australia, and Vienna, Austria), the present inventors have confirmed the oxidation of $H_2$ by soil, that this oxidation can be increased with exposure of the soil to $H_2$, and that $H_2$ oxidation capacity of soil increases with proximity to the root nodules of legumes. Soil oxidation of $H_2$ thus appears to be a global phenomenon and, insofar as such oxidation is carried out by soil microorganisms, the microorganisms must also exist globally. It is therefore expected that soils from virtually any location worldwide will exhibit some capacity to oxidize $H_2$, and that this capacity can be increased by exposing the soil to $H_2$. Also, the beneficial effect on crop growth of intercropping with legumes is recognized worldwide. However, to our knowledge, no studies have considered the effect of soil $H_2$ oxidation on the growth response of plants.

Some previous workers have attempted to understand the reasons that legume soils have the ability to enhance the growth of non-legume crops. For example, Fyson and Oaks (1990) concluded that fungi, rather than bacteria, were involved in the growth promotion. Others have attributed the enhancement to breaks in the disease cycle, or to the deep growth of legume roots that open channels in heavy soils that allow for subsequent growth of non-legume roots. No one has provided any evidence to suggest that the $H_2$ production by legume nodules potentiates enhanced growth or yield of plants.

It is apparent that previous research has been directed towards elucidating the kinetics of $H_2$ oxidation by soil, the nature of the organisms involved and the fate of the $H_2$ in soils. No studies have investigated or reported on the effects of soil, having been exposed to $H_2$, directly on the growth of plants. Further, no previous studies have linked $H_2$ production by legume nodules to the well known, beneficial effects of legumes in crop rotations.

According to a broad aspect of the invention, there is provided a method of enhancing plant growth or yield, wherein hydrogen gas ($H_2$) is applied to soil. As used herein, the term "soil" refers to any soil or soil-like composition capable of supporting plant growth. Thus, in accordance with the invention, there may be added to soil any number of additives or substitutes such as, but not limited to, mulch, peat moss, compost, sand, Vermiculite™, Promix™, Turface™, and Perlite™. Preferably, the soil employed is soil in which legumes have previously grown.

According to the invention, $H_2$ can be delivered to the soil via a pressurized source, such as a pressure tank, or a pump, and a distribution system such as tubing, the tubing buried in the soil and having outlet ports such as holes or nozzles appropriately sized and spaced to allow passage of the $H_2$ to the soil. The tubing may also be above the soil, and, for example, connected to nozzles or probes placed in the soil as required. A membrane having low permeability to $H_2$ can be placed over the soil, at least in the vicinity of the outlet ports or nozzles, to minimize any escape of $H_2$ to the atmosphere. In applications where $H_2$ is applied to soil in which crops are already planted, outlet ports or nozzles should be located as close as possible to the roots of the plants. For pretreatment of soil or soil substitutes later to be mixed with non-treated soil, the above methods can be used with soil placed in a container having low $H_2$ permeability. In such a container $H_2$ delivery can also be via, for example, holes or ports provided in the bottom and/or sides of the container. Such bulk treatment operations may also include apparatus to mix and/or vibrate the soil, either continuously or periodically, to facilitate $H_2$ contacting all of the soil.

The $H_2$ used can be bottled gas or it can be obtained via any other suitable process such as electrolysis of water or diluted acid (e.g., $H_3PO_4$), or from $H_2$ evolving (producing) microorganisms. Also, in some embodiments, the $H_2$ gas is provided dissolved in an appropriate solvent, e.g., aqueous. The source of $H_2$ to be used will depend on the particular application. For example, where $H_2$ is to be applied to crops in a field, a $H_2$ delivery system based on $H_2$ derived from electrolysis of water is appropriate. Such a system can employ wind and/or solar powered apparatus for production of $H_2$ via electrolysis and for delivery of the $H_2$ to a distribution network of tubing. Under certain conditions, such as appropriate moisture content of soil, it is also possible to generate $H_2$ directly in the soil by placing electrodes in the soil and passing an electric current therebetween. Such a system can conveniently be implemented in a field, for example, and employ wind/solar power. It is clear that systems for producing and delivering $H_2$ to soils and/or plants in accordance with the invention can be configured numerous ways.

The duration, flow rate and concentration of $H_2$ application to soil will depend on the amount of soil being treated and the optimal response of the soil in terms of its ability to enhance plant growth, and may be determined by a person of ordinary skill without undue experimentation. Similarly, conditions that optimize the plant growth response with minimal input costs for a particular soil/plant combination may be determined without undue experimentation. However, various treatments have been found which give a strong growth response. For example, $H_2$ may be applied at a concentration of 500 ppm (parts per million) and flow rate of 100 mL/min to a 1.5 L soil and sand mixture (v/v=2:1) (i.e., a rate of 0.134 µmole $H_2$/g dry mass of soil per h). The duration of such an application of $H_2$ is on the order of weeks, although shorter application durations are contemplated. Of course, the rate of $H_2$ delivery to the soil is not limited to the above example, and can be varied to suit any specific application. However, it is preferable that the rate of delivery of $H_2$ to the soil not exceed the soil's ability to consume (i.e., oxidize) the $H_2$, as any excess $H_2$ not oxidized would be wasted. Since the amount of $H_2$ that can be oxidized by soil increases with the duration of exposure of the soil to $H_2$, the rate of delivery of $H_2$ to the soil can be increased over time.

To obtain the enhanced growth response, $H_2$ can either be applied directly to the soil in which the plant is grown, or seeds or young plants can be placed into soils that have previously been treated with $H_2$, or into an untreated soil that contains a proportion of soil, either mixed or unmixed, that has previously been treated with $H_2$. For example, the proportion of soil previously treated with $H_2$ can range from about 5% to 100%. Consequently, the $H_2$ treatment may be carried out prior to planting or during any stage of plant growth. Preferably, the treatment is carried out prior to or early in plant growth to maximize the overall growth and/or yield enhancement.

It should be noted that the $H_2$-treated soil need not be mixed with existing soil to obtain the desired effect. For example, it is possible simply to place a depot of $H_2$-treated soil in close proximity to the roots of a plant, thereby introducing the treated soil while minimizing any disturbance to an already established plant. Also for example, a seed, germinated seed, seedling, or the like can be planted in a depot of $H_2$-treated soil within otherwise untreated soil. Similarly, during transplanting, a depot of $H_2$-treated soil can conveniently be placed in close proximity to the roots of plants.

When treating the soil with $H_2$, it is strongly preferred that the same soil be exposed to $H_2$ gas for an extended period, typically more than one week. In experiments in which about 2000 ppm $H_2$ was provided to 60 L of soil via a bank of nozzles, and in which the soil was completely mixed on a daily basis, the resulting soil had only minor plant growth promoting activity (data not shown). However, when similar soil was treated in the same way but without mixing, or with only gentle mixing once or twice a week, the resulting soil was very effective in promoting plant growth. These experiments would seem to indicate that the growth enhancing microorganisms require continuous exposure to $H_2$ to take on their plant growth enhancing characteristic, and mixing of the soil interrupts such exposure. This is supported by the fact that growth enhancing microorganisms, being adjacent to a legume nodule in the soil, would have continuous exposure to $H_2$ from the nodule.

According to another aspect of the invention there is provided a method for enhancing plant growth or yield, comprising obtaining an extract, such as an aqueous extract, from soil to which $H_2$ has been applied, and applying the extract to soil. The invention contemplates the application of such an extract to seeds, such that the seeds, upon planting, effectively introduce the desired plant growth-enhancing properties to the soil.

Legumes vary in the amount of $H_2$ that they deliver to soil, and in the volume of soil that they expose to $H_2$. For example, as discussed above, HUP+ symbioses can capture some or all of the $H_2$ that nitrogenase produces, such that many HUP+ symbioses loose little or no $H_2$ to the soil. Such symbioses are considered to be highly efficient with respect to $N_2$ fixation. On the other hand, HUP− symbioses can vary widely in their $H_2$ production relative to nitrogen fixation (Schubert and Evans, 1976). For the purposes of this invention, symbioses that are inefficient with respect to $N_2$ fixation produce about 2 to about 10 $H_2/N_2$, while efficient strains produce less than about $2H_2/N_2$.

The amount of $H_2$ that is delivered to soil and the volume of soil that is exposed to $H_2$ is also determined by the number and distribution of nodules on the root system of legumes, in addition to the rate that nodules produce $H_2$. For example, legumes that have most of their nodules in tightly packed clusters at the crown of their root system would expose a smaller volume of soil (albeit at a higher rate) than legumes that have nodules of similar activity distributed over their root system. There is evidence (Carroll et al. 1985, Qian et al. 1996) that legumes have genetic control over nodulation sites. Thus legumes with more nodules, relative to a wild-type plant of the same species, and/or a more even distribution of nodules over the root system, can be selected or engineered.

According to another aspect of the invention there is provided a method for enhancing plant growth or yield, comprising exposing soil to $H_2$ gas, wherein the $H_2$ gas is provided by a legume selected for its ability to produce $H_2$ gas. The legume can be planted prior to a target plant for which enhanced growth or yield is desired (i.e., crop rotation), or in the same field at the same time as the target crop (i.e., intercropping). The legume selected for its ability to produce $H_2$ gas can be a legume having HUP– nitrogen-fixing symbiotic bacteria, a legume having a type or strain of nitrogen-fixing symbiotic bacteria that is an inefficient nitrogen fixer, a legume that has an enhanced number of nodules, and/or a legume with distributed nodulation. Further, the legume selected for its ability to produce $H_2$ gas can be one having symbionts that have been genetically modified so as to be inefficient in fixing nitrogen, and/or one that has been genetically modified so as to have distributed modulation. Selecting a legume for its ability to produce $H_2$ gas in accordance with this aspect of the invention is contrary to traditional use of legumes for grain yield, crop rotation or intercropping, because traditionally, legumes have been selected for their ability to maximize $N_2$ fixation and hence minimize $H_2$ production (Eisbrenner and Evans, 1983).

As mentioned above, the mechanism by which $H_2$ fertilization of soils enhances plant growth is not yet fully understood, although there is much evidence suggesting that $H_2$ oxidizing microorganisms in the soil potentiate enhanced plant growth or yield. This may occur through a direct mechanism. Alternatively, there may be a series of events or actors between the application of $H_2$ and the enhanced plant growth or yield. Recent experimental results demonstrate increased growth of certain bacteria, indicated by the presence in soil of prominent colonies, upon exposure of the soil to $H_2$. Preliminary investigation revealed these colonies to be made from a filamentous bacteria in white or yellow colonies. Soil samples containing the colonies were serially diluted with sterile water and colonies were grown on either a mineral salt medium or on a soil extract medium in the presence of 10% $H_2$ and 5% $CO_2$ in air. Single colonies were isolated, transferred to another culture under the same conditions, and tested for their ability to oxidize $H_2$ gas. Colonies that oxidize $H_2$ were isolated, and they are expected to potentiate plant growth when applied to soil not treated with $H_2$.

The invention thus contemplates a method for enhancing plant growth or yield, involving applying $H_2$ oxidizing microorganisms to soil, seeds, or roots of plants. In accordance with the invention the $H_2$ oxidizing microorganisms can be isolated from soil samples exposed to $H_2$ as described above. The $H_2$ oxidizing microorganisms can be cultured, and represent the most efficient way to obtain the enhanced plant growth or yield provided by the invention. Of course, $H_2$ can be applied directly to cultures of $H_2$ oxidizing soil microorganisms to increase the growth of the microorganisms prior to application to soil, seeds, and plant roots.

The contents of all scientific publications cited in this application are incorporated herein by reference.

The present invention is further described by way of the following examples.

EXAMPLE 1

Barley Growth Response

Soils were obtained from three locations in or near Kingston, Ontario Canada: under lawn grass (O), from a hay field (F), and from a home garden (G). Each soil was mixed with sand (soil:sand=2:1), and six 1.5 L pots were filled with each type of soil:sand mixture (hereinafter referred to as soil). Three 1.5 L pots of each soil type were randomly selected for treatment with $H_2$, and the remaining three 1.5 L pots of each soil type were controls and treated with air. In the $H_2$ treatment, $H_2$ was produced by electrolysis of 100 mM$H_3PO_4$ and provided to a continuously flowing air stream to give a concentration of 500 ppm. Each 1.5 L pot received 100 mL/min for 47 days while the concentration of $H_2$ entering and leaving the pot was monitored using a $H_2$ gas sensor (Layzell et al. 1984). The air treatment was identical except there was no electrolysis and the $H_3PO_4$ was replaced by water.

After the 47 d pretreatment, the soil was thoroughly mixed within each treatment ($H_2$ or air) and distributed into three 500 mL pots. Two days later, nine barley seeds were planted in each pot, and the pots were watered daily with tap water. Thirty-eight days after planting, the barley plants for each soil type and treatment were harvested for analysis of dry mass of root and shoot. Plants were dried to constant mass at 80° C.

Figure 1:
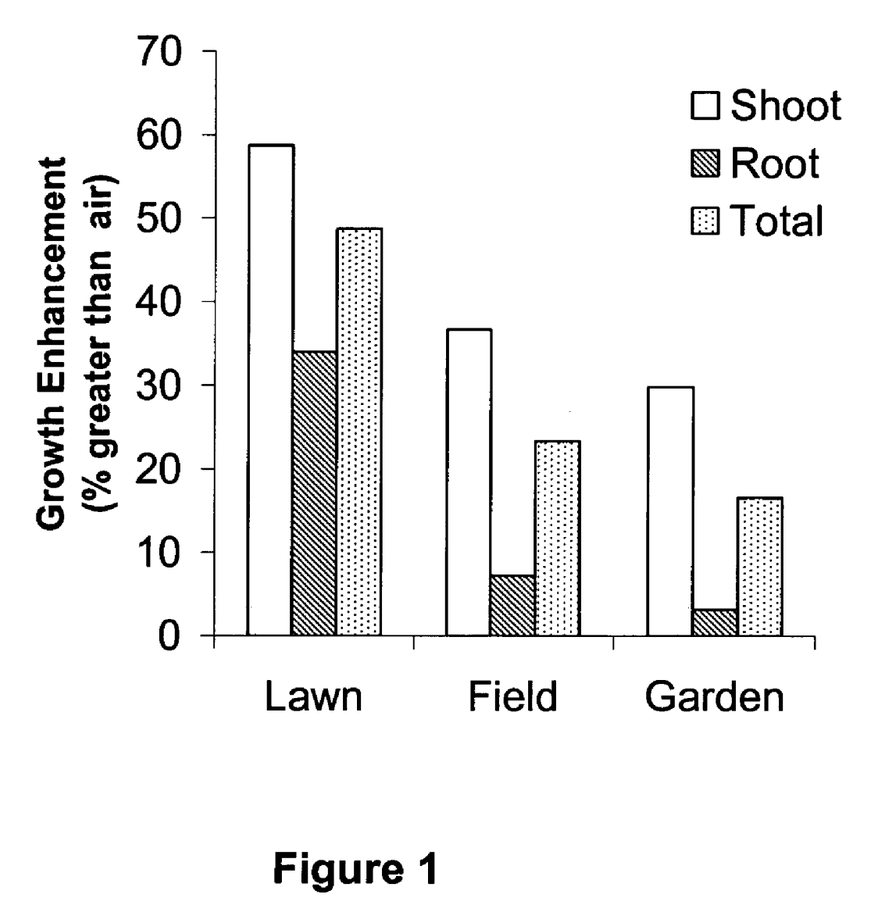
FIG. 1 shows the growth response of barley to air- or $H_2$-treated soil from three locations, in terms of dry mass of root and shoot, after 38 and 48 days growth.

At 38 d after sowing, the dry weight of the barley plants from the $H_2$ treated soils were 17 to 49% greater than those in the air treated soils (FIG. 1), with the shoots accounting for the majority of the growth enhancement (Table 1). The soils taken from under lawn grass showed the greatest growth enhancement with $H_2$ (49%) while the garden soil showed the least (17%). Among the air treatments, the plants grown in the garden soil were the greatest, suggesting that the $H_2$ treatment was particularly effective on poor soils.

TABLE 1

Dry weight comparisons of barley (per plant).

| Soil Treatment | | Shoot Mean ± SE (gDW) | p value of t-test | Growth enhance | Root Mean ± SE (gDW) | p value of t-test | Growth Enhance |
|---|---|---|---|---|---|---|---|
| Lawn | Air | 0.98 ± 0.02 | *0.000066 | | 0.68 ± 0.03 | | |
|  | $H_2$ | 1.56 ± 0.02 | | 58.98% | 0.91 ± 0.06 | **0.04996 | 33.99% |
| Field | Air | 1.07 ± 0.05 | *0.01533 | | 0.88 ± 0.02 | | |
|  | $H_2$ | 1.47 ± 0.07 | | 36.65% | 0.95 ± 0.08 | 0.4925 | 7.71% |
| Garden | Air | 1.55 ± 0.02 | *0.000341 | | 1.55 ± 0.03 | | |
|  | $H_2$ | 2.02 ± 0.03 | *0.000341 | 29.83% | 1.60 ± 0.03 | 0.3085 | 3.23% |

*Significant different at 99%,
**Significant different at 95%.

EXAMPLE 2

Growth Response of Soybean, Barley and Canola

Field soil obtained near Kingston, Ontario Canada was mixed with sand (soil:sand 2:1), and 50 L of the soil:sand mixture (hereinafter referred to as soil) was placed into each of two containers. One of the containers was treated with $H_2$ (500 ppm, supplied from a compressed tank of high purity gas) in an air stream, the other with air alone. The flow rate of air or $H_2$ was initially 2.5 L/min per container. After 22 days, the concentration of $H_2$ was increased to 1000 ppm, and after a further 7 days, it was increased to 2000 ppm. During exposure to air or $H_2$, the soil was mixed every 5 days. Both the air and $H_2$ application were stopped 65 days from commencement, and 14 days later 500 mL pots were filled with air- or $H_2$-pretreated soil and randomly assigned to one of five nutrient regimes: +NPK; −N +PK; −P, +NK; −K, +NP; −NPK where N was provided at 0.06 g N/pot, P at 0.05 g $P_2O_5$/pot and K at 0.06 g $K_2O$/pot.

The fertilizers were completely mixed with the soil prior to planting seeds. Six pots were used for each treatment. Within each pot a single crop was planted, involving either 9 barley seeds, 5 canola seeds or 4 soybean seeds. Plants were watered daily with tap water, harvested 41 or 42 days after planting, and dried to constant mass for analysis of dry mass of root and shoot.

Figure 2:
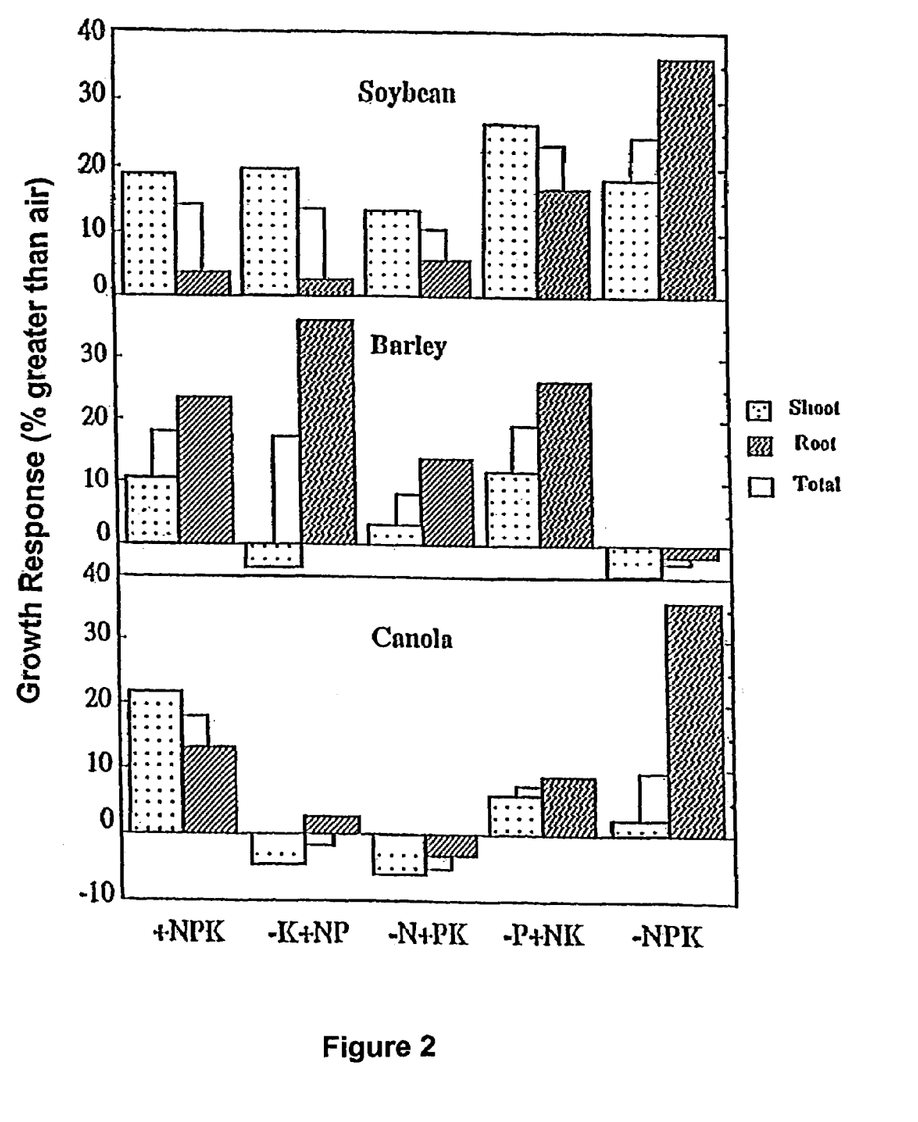
FIG. 2 shows the growth response of soybean, barley, and canola to air- or $H_2$-treated soil under different nutrient regimes, in terms of dry mass of root and shoot, after 41 to 42 days growth.

As can be seen from FIG. 2, all three crop species exhibited enhanced growth (15–19%) in terms of dry mass, of root and/or shoot, when the soil was pretreated with $H_2$ and the plants were provided with all of their nutritional requirements. However, in some cases, such as that of canola under N or K deprivation, there was no effect of $H_2$ pretreatment.

EXAMPLE 3

Soil Extract

Field soil obtained near Kingston, Ontario Canada was treated with air or $H_2$ in air as in example 2. Then, 1 L of loosely packed soil was extracted with 1 L of distilled water. The water and soil were mixed for about a minute and allowed to settle for 5 minutes (repeat 2×). The extract was removed, strained through a series of sieves and then cheese cloth and left to settle over night. A fine silt settled to the bottom and the clear extract was used in the experiments. Barley seeds were planted into 30 mL of unextracted field soil which were given 30 mL of soil extract, of which 0, 1 or 3 mL were obtained from the $H_2$ treated soils. The remaining extract was obtained from the air treated soils. Thereafter, barley plants were watered with tap water and fertilized with 20:20:20 once per week. They were harvested after 25 days of growth, and dried to constant mass at 70° C.

The results (Table 2) showed that a significant growth enhancement of 28% for roots, and 36% for shoots was obtained when 3 mL of extract was provided to the soil at sowing.

TABLE 2

The effect of an aqueous extract of $H_2$ treated soil on the dry weight of barley roots and shoots. Values are presented as mean +/− standard error (SE) (N = 11).

| Extract of | | Shoot | | Root | |
| --- | --- | --- | --- | --- | --- |
| Air treated Soil (mL) | $H_2$ treated soil (mL) | Mean ± SE (gDW/pl) | Growth enhancement | Mean ± SE (gDW/pl) | Growth enhancement |
| 30 | 0 | 0.0708 ± 0.0043 | | 0.0535 ± 0.0041 | |
| 29 | 1 | 0.0811 ± 0.0061 | 14.6% | 0.0601 ± 0.0032 | 12.3% |
| 27 | 3 | 0.0960 ± 0.0054 | *35.6% | 0.0683 ± 0.0049 | *27.7% |

*Significant different at $p \leq 0.05$.

EXAMPLE 4

Spring Wheat Growth Response

Field soil from a farm in the Annapolis Valley, Nova Scotia was mixed with fine clear filter sand (soil:sand=2:1), and 50 L of the soil:sand mixture was placed into each of two containers. One of the containers was treated with $H_2$ (2000 ppm, supplied from a compressed tank of high purity gas) in an air stream, the other with air alone. The flow rate of air or $H_2$ was 2 L/min per container. The treatment was stopped after 30 days and used immediately for spring wheat growth experiments. The soils were put into green plastic seedling trays (9 pack) with each pot holding 60 mL soil mixture and one spring wheat seed. Plants were watered with 1/10 Hoagland solution with 5 mM $NH_4NO_3$ daily, and then harvested at 30 days and dry weight of the roots and shoots were recorded.

As can be seen in Table 3, the growth of both root and shoot of spring wheat were more than 30% greater ($p \geq 0.01$) in the $H_2$ treated soil than in the air treated soil.

TABLE 3

The effect of $H_2$ pretreatment of soil on the biomass of spring wheat after 30 d of growth in that soil. Values are presented as mean +/− standard error (N = 18).

| | Air treatment (gDW/plant) | $H_2$ treatment (gDW/plant) | Enhancement |
| --- | --- | --- | --- |
| Shoot | 0.116 ± 0.006 | 0.152 ± 0.004 | 31.1% |
| Root | 0.031 ± 0.001 | 0.041 ± 0.001 | 34.1% |
| Total | 0.147 ± 0.007 | 0.193 ± 0.004 | 31.7% |

EXAMPLE 5

Soil Inoculate

Soil was obtained from a farm in the Annapolis Valley, Nova Scotia. Soil was mixed with fine clear filter sand (soil:sand=2:1). Two glass tubes (diameter 3.3 cm, length 123 cm) were filled with the soil:sand mixture. One tube was treated with hydrogen (2000 ppm, supplied from a compressed tank of high purity gas) in an air stream, the other with air alone. The flow rate of air or hydrogen was about 150 mL/min per tube. Both the air and hydrogen applications were stopped at 44 days, and used immediately for wheat growth experiments.

Soils and Promix were mixed thoroughly by a ratio of 1:19 (v/v). The green plastic seedling trays (9 packs) were used to grow spring wheat. Each pot held about 60 mL soil-Promix mixture. Spring wheat seeds were soaked between wet paper towel in Petri dishes for 2 days. One seed was planted in each pot. Plants were watered daily with 1/10 strength Hoagland solution with 5 mM $NH_4NO_3$. Plants were harvested 35 days after planted. At 35 days, the dry weight of spring wheat plants inoculated with $H_2$ treated soil were about 20% greater than those with air treated soil (Table 4). In addition, the plants grown in the $H_2$ treated soil formed their ear about two to three days earlier than plants grown in air treated soils.

TABLE 4

The effect of a 5% mixture of $H_2$ treated soils on the biomass of Spring wheat after 35 d of growth. Values are presented as mean +/− standard error (N = 72).

|  | Air Treatment gDW/pl (mean ± SE) | $H_2$ Treatment gDW/pl (mean ± SE) | Sig. Diff (p) | Growth Enhancement |
|---|---|---|---|---|
| Shoot | 0.311 ± 0.014 | 0.373 ± 0.013 | 0.0017 | 19.88% |
| Root | 0.057 ± 0.004 | 0.071 ± 0.002 | 0.0019 | 24.42% |
| Total | 0.3678 ± 0.017 | 0.444 ± 0.014 | 0.0012 | 20.58% |

EXAMPLE 6

Fungicide Application

Field soil obtained from a farm in the Annapolis Valley, Nova Scotia was treated and mixed with Promix as in Example 5. Some soils were treated with the fungicide Benomyl™ (36 mg/L), a common seed treatment used in agriculture. Plastic seedling trays (9 pack) were provided with about 60 mL soil-Promix mixture and one spring wheat seed was sown after being germinated for 2 days between wet paper towel in a Petri dish. Plants were watered daily with 1/10 strength Hoagland solution containing 5 mM $NH_4NO_3$ and harvested at 35 days after planted.

The fungicide Benomyl improved spring wheat growth in both air or $H_2$ treated soils (Table 5, 6 and 7). The experiment suggests that fungicide coating of many commercial crop seeds will not impair the effect of $H_2$ treatment of soil and vice versa. In fact, the growth enhancement of Benomyl and $H_2$ fertilization may be additive (Table 5). The hydrogen uptake ability of soil was not affected by Benomyl (data not shown).

TABLE 5

The effect of Benomyl and $H_2$ pretreatment of soils on the biomass of spring wheat after 35 d of growth. Values are presented as mean +/− standard error.

| Treatment | Total DW (gDW/plant) | Growth Enhancement |
|---|---|---|
| Air Alone | 0.368 ± 0.01746 | — |
| Air + Benomyl | 0.396 ± 0.02116 | 7.5% |
| $H_2$ Alone | 0.444 ± 0.01422 | 20.6% |
| $H_2$ + Benomyl | 0.456 ± 0.01745 | 24.0% |

TABLE 6

The effect of Benomyl + $H_2$ pretreatment of soils on the biomass of shoots and roots of spring wheat after 35 d of growth. Values are presented as mean +/− standard error.

|  | Air Treatment (gDW/pl) | $H_2$ + Benomyl Treatment (gDW/pl) | Sig. Diff (p) | Growth Enhancement |
|---|---|---|---|---|
| Shoot | 0.311 ± 0.014 | 0.3822 ± 0.015 | *0.0010 | 22.81% |
| Root | 0.057 ± 0.004 | 0.0740 ± 0.003 | *0.0005 | 30.41% |
| Total | 0.368 ± 0.017 | 0.4562 ± 0.017 | *0.0006 | 23.99% |

TABLE 7

The effect of $H_2$ pretreatment of Benomyl treated soils on the biomass of shoots and roots of spring wheat after 35 d of growth. Values are presented as mean +/− standard error.

|  | Air + Benomyl Treatment (gDW/pl) | $H_2$ + Benomyl Treatment (gDW/pl) | Sig. Diff (p) | Growth Enhancement |
|---|---|---|---|---|
| Shoot | 0.338 ± 0.018 | 0.382 ± 0.015 | 0.068 | 13.26% |
| Root | 0.058 ± 0.004 | 0.074 ± 0.003 | *0.002 | 27.34% |
| Total | 0.396 ± 0.021 | 0.456 ± 0.017 | *0.033 | 15.33% |

EXAMPLE 7

Growth Response

Methods were similar to those of Example 2, above. Briefly, field soil from Vienna, Austria was mixed with sand (soil:sand=2:1), and the soil:sand mixture (hereinafter referred to as soil) was placed into each of two containers. One of the containers was treated with $H_2$ (500 ppm) in an air stream, the other with air alone. The flow rate of air or $H_2$ was initially 1.25 L/min per container. During exposure to air or $H_2$, the soil was mixed every day. At the end of the air and $H_2$ application, pots were filled with air- or $H_2$-pretreated soil. Canola, corn, barley, and soybean seeds were planted. Plants were watered regularly and fertilized. Data recorded included number of days to first flower, and dry biomass. Data have not yet been analyzed in detail; however, it was clear that the corn and canola grown in $H_2$-treated soil had fewer days to first flower and greater biomass than the plants grown in air-treated soil. The inventors believe that still better results would have been achieved if the soil was not mixed on a daily basis. The barley and soybean plants were inadvertently overfertilized and as a result no data were obtained for those species.

EXAMPLE 8

Field Trials

Soils from fields in Minto, Manitoba (MB) and at the Nova Scotian Agricultural College, Truro, Nova Scotia (NS) were placed in 70 L plastic containers and provided with 3 to 5 L/min of either air, or an air-$H_2$ mixture (exposure rate of up to 250 μmoles $H_2$/L soil/h). After 1 to 2 weeks of exposure, the $H_2$ uptake activity of the $H_2$-treated soil increased sharply, as measured by a hydrogen gas analyzer (model S121, Qubit Systems Inc., Kingston, Ontario). Once the $H_2$-treated soil consumed 250 μmoles $H_2$/L/h, it was provided with this exposure rate for an additional 3 weeks.

After about 5 weeks, the air- and $H_2$-treated soils were mixed separately and used the next day in field trials at the above locations for barley (MB and NS) and spring wheat (MB only). For each crop, a random block design was used involving 4 (MB) or 5 (NS) replicates of three treatments: air-treated soil, $H_2$-treated soil, and untreated soil (control). A V-shaped trough was made at 15 cm intervals, and the treated or untreated soils were placed in the bottom of the trough at a rate of about 230 mL soil/m row (1.65 L treated soil per m$^2$) in NS and 950 mL soil/m row (6.4 L treated soil per m$^2$) in MB. Wheat seeds were planted at a density of 120 kg/ha and barley seeds at a density of 150 kg/ha in MB. In the NS plots, barley seeds were planted at a density of approximately 140 kg/ha. All seeds were hand planted and in MB, fertilizer (20-20-20) added with seeds at a rate of 100 kg/ha. The seeds were then covered with field soil. In NS, fertilizer (17-17-17) was broadcast and raked into the soil prior to making the trough at a rate of 300 kg/ha.

In MB, tiller numbers per plant were counted after 7 weeks, whereas in NS the number of heads were counted per 2 m row after 8 weeks of growth (Table 8). No effect was observed between the control and air-treated soils. However, the barley and spring wheat seeds planted in $H_2$-treated soil displayed tiller head numbers that were 36% to 48% higher than in the air-treated or control soils.

TABLE 8

The effect of planting seeds in soils pretreated with $H_2$ gas on the number of tillers present in barley or spring wheat (MB) or in the number of heads produced per 2 m row of barley (NS).

| Treatment | MB (7 weeks) | | NS (8 weeks) |
|---|---|---|---|
| | Barley (# tillers/plant) | Spring Wheat (# tillers/plant) | Barley (# heads/2 m row) |
| Control | 4.9 ± 0.17 | 6.5 ± 0.32 | 120 ± 8 |
| Air | 4.8 ± 0.15 | 6.4 ± 0.24 | 120 ± 8 |
| $H_2$ | 6.6 ± 0.20 | 9.4 ± 0.33 | 170 ± 14 |
| % Increase ($H_2$ over air) | 36% | 48% | 42% |

Greater tiller and head numbers observed in the plants grown in $H_2$-treated soils are expected to lead to a significantly greater yield than those grown in field soil. The minimum amount of $H_2$-treated soil needed to optimize yields, and whether a longer pretreatment of soil with $H_2$ will increase its potency in enhancing the growth and yield of crops, can be determined through routine experimentation, currently in progress.

Those skilled in the art will recognize, or be able to ascertain through routine experimentation, equivalents to the specific embodiments described herein. Such equivalents are considered to be within the scope of this invention and are covered by the appended claims.

REFERENCES

Bankole, S. A. and Adebanjo, A. 1996. Crop Protection, 15:633–636.
Bolton, E. F., et al. 1976. Canadian Journal of Soil Sciences, 56:21–25.
Brown, M. E. 1974. Annu. Rev. Phytopathol. 12:181–197.
Carroll, B. J, et al. 1985. Plant Physiol. 78:34–40.
Conrad, R., et al. 1979a. Soil Biol. Biochem. 11:689–690.
Conrad, R., et al. 1979b. FEMS Microbiol. Let. 6:143–145.
Conrad, R., et al. 1980. Geophys. Res. 85:5493–5498.
Conrad, R., et al. 1983. FEMS Microbiol. Let. 18:207–210.
Conrad, R. 1988. Adv. Microb. Ecol. 10:231–384.
Cook, R. I. 1993. Annu. Rev. Phytopathol. 31:53–80.
Dugnani, L., et al. 1986. FEMS Microbiol. Ecol. 38:347–352.
Eisbrenner, G., and Evans, H. J. 1983. Ann. Rev. Plant Physiol. 34:105–136.
Fyson, A. and Oaks, A. 1990. Plant and Soil, 122:259–266.
Glick, B. R. 1995. Can. J. Microbiol. 41:109–117.
Haring, V. and Conrad R. 1994. Biol. Fertile Soils, 17:125–128.
Hart, P. B. S., et al. 1986. New Zealand Journal of Agricultural Research, 29:681–686.
Hesterman, O. B., et al. 1986. Agron. J. 78:19–23.
Insam, H., et al. 1991. Soil Biology and Biochemistry, 23:459–464.
Kloepper, J. W., et al. 1988. ISI Atlas Sci. Anim. Plant Sci. pp. 60–64.
Kloepper, J. W., et al. 1989. Trends Biotechnol. 7:39–43.
Kluber, H. D., et al. 1995. FEMS Microbiol. Ecol. 16:167–176.
La Favre, J. S., et al. 1983 Appl. Environ. Microbiol. 46:304–311.
Layzell, D. B., et al. 1984. Plant Physiol. 75:582–585.
Lechner, S. and Conrad, R. 1997. FEMS Microbiol. Ecol. 22:193–206.
Omar, S. A. and AbdAlla, M. H. 1998. Folia Microbiologica, 43:431–437.
O'Sullivan, D. J., and O'Gara, F. 1992. Microbiol. Rev. 56:662–676.
Popelier, et al. 1985. Plant and Soil 85:85–96.
Qian, D., et al. 1996. Crop Sci. 36:243–249.
Schubert, K. R. and Evans, H. J. 1976. Proc. Natl. Acad. Sci. USA 73:1207–1211.
Schuler, S., et al. 1991a. Biol. Fert. Soils 11:190–195.
Schuler, S., et al. 1991b. Biol. Fert. Soils 12:127–130.
Sivan, A. and Chet, I. 1992. In Environmental Microbiology. Edited by R. Mitchell. Wiley-Liss, Inc., New York. pp. 335–354.
Srivastava, S. C. and Singh, J. S. 1991. Soil Biology and Biochemistry, 23:117–124.
Williams, B. L. and Sparling, G. P. 1988. Soil Biology and Biochemistry, 20:579–581.

We claim:

1. A method for enhancing plant growth or yield, comprising:
    treating soil with $H_2$ gas:
        (i) at a concentration at least 50 times greater than the concentration of $H_2$ in air; and
        (ii) for a duration sufficient to increase $H_2$ uptake of the soil;
    obtaining an extract of the soil treated with $H_2$ gas; and
    applying the extract to seeds, plant roots, or soil;
    wherein growth or yield of a plant from said seeds or plant roots or in said soil is enhanced.

2. The method of claim 1, wherein the extract is an aqueous extract.

3. The method of claim 1, wherein the concentration of $H_2$ gas is 500 to 4000 times greater than the concentration of $H_2$ gas in air.

4. The method of claim 1, wherein the concentration of $H_2$ gas provided is increased as treatment of soil progresses.

5. The method of claim 1, wherein the duration is at least 1 week.

6. The method of claim 1, wherein the duration is between 1 week and 10 weeks.

7. The method of claim 1, wherein said treating soil with $H_2$ gas enhances the ability of soil microorganisms to oxidize $H_2$.

8. A soil extract for enhancing plant growth or yield, the extract prepared by a method comprising:
  treating soil with $H_2$ gas:
    (i) at a concentration at least 50 times greater than the concentration of $H_2$ in air; and
    (ii) for a duration sufficient to increase $H_2$ uptake of the soil; and
  obtaining the extract from the soil treated with $H_2$ gas;
  wherein, when the extract is applied to seeds, plant roots, or soil, growth or yield of a plant from said seeds or plant roots or in said soil is enhanced.

9. The soil extract of claim 8, wherein the soil extract is aqueous.

10. The soil extract of claim 8, wherein said treating soil with $H_2$ gas enhances the ability of soil microorganisms to oxidize $H_2$.

11. The soil extract of claim 10, wherein the extract comprises said soil microorganisms.

12. The soil extract of claim 8, wherein the concentration of $H_2$ gas is 500 to 4000 times greater than the concentration of $H_2$ gas in air.

13. The soil extract of claim 8, wherein the concentration of $H_2$ gas provided is increased as treatment of soil progresses.

14. The soil extract of claim 8, wherein the duration is at least 1 week.

15. The soil extract of claim 8, wherein the duration is between 1 week and 10 weeks.

* * * * *